(12) United States Patent
Hung

(10) Patent No.: US 10,485,636 B2
(45) Date of Patent: Nov. 26, 2019

(54) ORTHODONTIC BRACKET

(71) Applicant: Cheng-Hsiang Hung, New Taipei (TW)

(72) Inventor: Cheng-Hsiang Hung, New Taipei (TW)

( * ) Notice: Subject to any disclaimer, the term of this patent is extended or adjusted under 35 U.S.C. 154(b) by 0 days.

(21) Appl. No.: 15/827,184

(22) Filed: Nov. 30, 2017

(65) Prior Publication Data

US 2019/0090987 A1    Mar. 28, 2019

Related U.S. Application Data

(60) Provisional application No. 62/563,771, filed on Sep. 27, 2017.

(51) Int. Cl.
*A61C 7/28* (2006.01)
*A61C 7/14* (2006.01)
*A61C 7/20* (2006.01)
*A61C 7/02* (2006.01)

(52) U.S. Cl.
CPC .............. *A61C 7/28* (2013.01); *A61C 7/20* (2013.01); *A61C 7/02* (2013.01); *A61C 7/141* (2013.01); *A61C 7/145* (2013.01)

(58) Field of Classification Search
CPC .. A61C 7/12; A61C 7/125; A61C 7/14; A61C 7/143; A61C 7/145; A61C 7/148; A61C 7/16; A61C 7/28; A61C 7/285
USPC ...................................................... 433/8–17
See application file for complete search history.

(56) References Cited

U.S. PATENT DOCUMENTS

| | | | | |
|---|---|---|---|---|
| 3,043,007 A | * | 7/1962 | Wallshein | A61C 7/12 433/20 |
| 3,158,934 A | | 12/1964 | Waldman | |
| 3,218,713 A | * | 11/1965 | Wallshein | A61C 7/12 433/11 |
| 4,936,774 A | * | 6/1990 | Stoller | A61C 7/12 433/110 |

(Continued)

FOREIGN PATENT DOCUMENTS

| | | |
|---|---|---|
| CN | 202821674 U | 3/2013 |
| JP | 2012-095994 A | 5/2012 |

(Continued)

OTHER PUBLICATIONS

European Patent Office, Search Report, Application No. 18197189.6, dated Jan. 29, 2019, Europe.

*Primary Examiner* — Wade Miles
*Assistant Examiner* — Matthew P Saunders

(57) ABSTRACT

An orthodontic bracket is provided, including a backend surface, a frontend surface, a first side surface, a second side surface, and a passageway. The backend surface is adapted for attachment and is opposite the frontend surface. The first and second side surfaces are connected between the backend surface and the frontend surface. The passageway extends from the first side surface to the second side surface. The cross-section of the passageway includes an access opening, an archwire slot, a path portion, and at least one rotation portion. The access opening is configured to allow the archwire to enter the passageway. The archwire slot is configured to receive the archwire. The path portion connects the access opening and the archwire slot. The rotation portion is provided in the path portion to allow the archwire to change its orientation.

15 Claims, 16 Drawing Sheets

(56) References Cited

U.S. PATENT DOCUMENTS

| | | | |
|---|---|---|---|
| 9,517,112 B2 * | 12/2016 | Hagelganz | A61C 7/12 |
| 2006/0263737 A1 * | 11/2006 | Oda | A61C 7/12 433/10 |
| 2016/0235502 A1 | 8/2016 | Hagelganz et al. | |
| 2017/0325912 A1 * | 11/2017 | Feller | A61C 7/12 |

FOREIGN PATENT DOCUMENTS

| | | | | |
|---|---|---|---|---|
| WO | WO 2016066514 A1 * | 5/2016 | | A61C 7/02 |
| WO | WO 2017109716 A1 * | 6/2017 | | A61C 7/143 |

* cited by examiner

US 10,485,636 B2

ORTHODONTIC BRACKET

CROSS REFERENCE TO RELATED APPLICATIONS

The present application claims priority of U.S. Provisional Patent Application No. 62/563,771, filed on Sep. 27, 2017, the entirety of which is incorporated by reference herein.

BACKGROUND OF THE INVENTION

Field of the Invention

The present application relates to an orthodontic correction technology; and in particular to an orthodontic bracket designed to receive orthodontic archwires.

Description of the Related Art

Misaligned teeth can adversely affect a person's dental aesthetics, functions, and health. The goal of orthodontic correction is to bring the teeth into proper alignment by using appliances which exert mechanical forces to move the teeth to positions or orientations where the dental functions and aesthetics are improved.

Conventional braces use archwires and brackets to induce corrective force on the teeth. The archwire is pre-shaped and interconnects the teeth through brackets that are fixed to the surfaces of the teeth. When initially installed, the archwire elastically deforms to accommodate the misaligned teeth. The archwire is resilient and exerts forces on the teeth through the brackets to bring the teeth into alignment with the pre-shaped form of the archwire. The archwire exerts continuous forces on the teeth to urge them to their finish positions. Traditional wires are fixed to the brackets using ligatures and strong forces are transmitted to the teeth. With self-ligating brackets, archwires can slide more freely in the bracket slot, achieving orthodontic tooth movement with less pressure and discomfort to the patient.

Prior art discloses self-ligating brackets consisting of a main bracket body attached to a base. An archwire slot extends mesial-distally across the main bracket body and between the gingival and occlusal tie wings. The archwire slot opens edgewise in the opposite direction to the base to receive an archwire. The bracket further consists of a locking clip which allows placement and removal of an archwire in the open position and slides to lock in place to maintain the archwire in the archwire slot in the closed position. Prior art discloses various locking clips or closures designed to achieve the same purpose.

Installation of the archwire with the self-ligating brackets requires specialized tools designed to manipulate the opening and closing of the locking clips or closures. Usually, the placement and removal of an archwire is performed by a person (e.g. dentist) other than the patient who is not able to perform the task alone. Such manipulations can be difficult, especially in the case of lingual brackets. The locking clips or closures add to the complication and cost in the manufacture of the self-ligating brackets. The structure of the locking clips or closures also add edges and protrusions to the bracket body which causes more discomfort to the patient.

It is desirable to make the task of archwire installation easier with an improved bracket design without a locking clip or closure mechanism. The present invention improves upon the deficiencies in prior art devices by simplifying the design and construction of the bracket while retaining the archwire retention characteristics of self-ligating brackets.

BRIEF SUMMARY OF THE INVENTION

In some embodiments of the invention, an orthodontic bracket for use in combination with an archwire to apply corrective force to a tooth is provided. The orthodontic bracket includes a backend surface, a frontend surface, a first side surface, a second side surface, and a passageway. The backend surface is adapted for attachment. The frontend surface is opposite the backend surface. The first side surface is connected between the backend surface and the frontend surface. The second side surface is connected between the backend surface and the frontend surface and opposite the first side surface. The passageway extends from the first side surface to the second side surface. The cross-section of the passageway includes an access opening, an archwire slot, a path portion, and at least one rotation portion. The access opening is configured to allow the archwire to enter the passageway. The archwire slot is formed at the end of the passageway to receive the archwire. The path portion connects the access opening and the archwire slot. The rotation portion is provided in the path portion to allow the archwire to change its orientation.

In some embodiments of the invention, an orthodontic bracket for use in combination with an archwire to apply corrective force to a tooth is provided. The orthodontic bracket includes a backend surface, a frontend surface, a first side surface, a second side surface, and a passageway. The backend surface is adapted for attachment. The frontend surface is opposite the backend surface. The first side surface is connected between the backend surface and the frontend surface. The second side surface is connected between the backend surface and the frontend surface and opposite the first side surface. The passageway extends from the first side surface to the second side surface. The cross-section of the passageway includes an access opening, an archwire slot, and a path portion. The access opening is configured to allow the archwire to enter the passageway. The archwire slot is formed at the end of the passageway to receive the archwire. The path portion connects the access opening and the archwire slot and has a curved form.

In some embodiments of the invention, an orthodontic bracket for use in combination with an archwire to apply corrective force to a tooth is provided. The orthodontic bracket includes a backend surface, a frontend surface, a first side surface, a second side surface, and a passageway. The backend surface is adapted for attachment. The frontend surface is opposite the backend surface. The first side surface is connected between the backend surface and the frontend surface. The second side surface is connected between the backend surface and the frontend surface and opposite the first side surface. The passageway extends from the first side surface to the second side surface. The cross-section of the passageway includes an access opening, an archwire slot, a path portion, and at least one notch. The access opening is configured to allow the archwire to enter the passageway. The archwire slot is formed at the end of the passageway to receive the archwire. The path portion connects the access opening and the archwire slot. The at least one notch is formed on the first side surface and/or the second side surface for retaining an O-ring elastic.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1A:
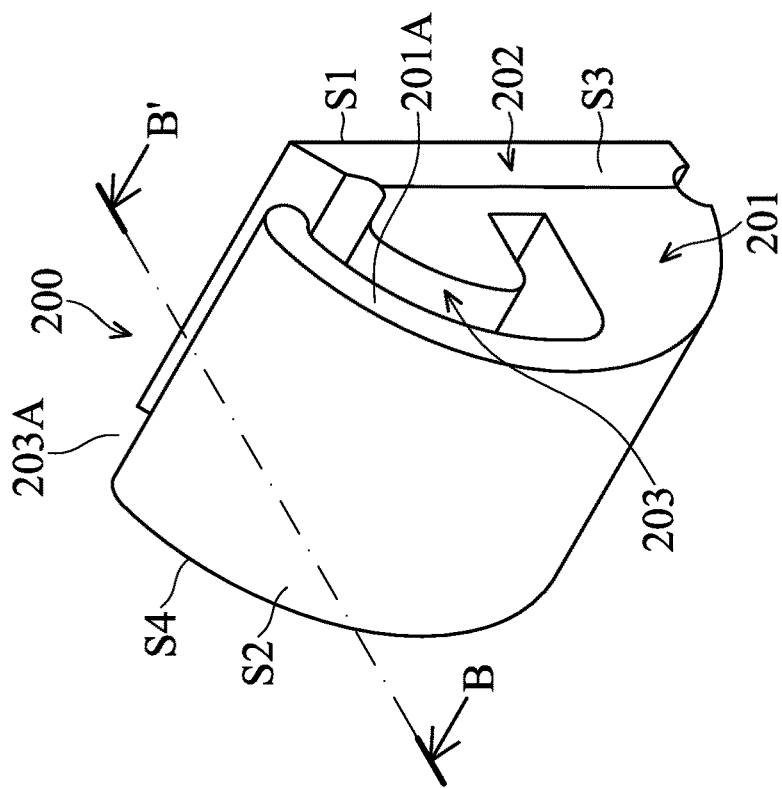
FIG. 1A is a perspective view illustrating a pair of counteracting brackets according to some embodiments of the present invention.
Figure 1A:
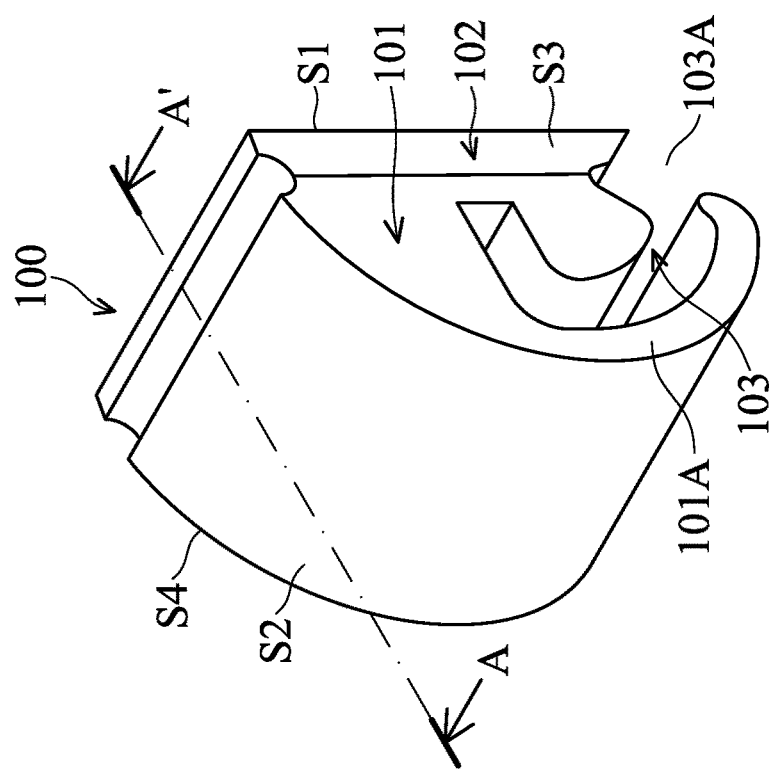

In order to illustrate the purposes, features, and advantages of the invention, the preferred embodiments and drawings of the invention are shown in detail as follows.

In the following detailed description, the orientations of "on", "above", "under", "below", "left", and "right" are used for representing the relationship between the relative positions of each element as illustrated in the drawings, and are not meant to limit the invention.

Moreover, although the terms first, second, third, fourth etc. may be used in the following detailed description to describe various elements, regions or sections, these elements, regions or sections should not be limited by these terms. These terms are only used to distinguish one element, region or section from another element, region or section. Thus, a first element, region or section discussed below could be termed a second element, region or section without departing from the teachings of the present invention.

In addition, the present disclosure may repeat reference numerals and/or letters in the various examples. This repetition is for the purpose of simplicity and clarity and does not in itself dictate a relationship between the various embodiments and/or configurations discussed. Various features may be arbitrarily drawn in different scales for the sake of simplicity and clarity.

Embodiments of the present invention disclose an orthodontic bracket design with a locking system that does not use a locking clip or closure for entrapping an archwire in the archwire slot. The locking system requires the deployment of at least two counteracting (orthodontic) brackets. FIG. 1A is a perspective view illustrating a pair of counteracting brackets according to some embodiments of the present invention. The top of the figure points to the occlusal direction, and the bottom of the figure points to the gingival direction. The pair of counteracting brackets includes a gingival access bracket 100 and an occlusal access bracket 200.

The gingival access bracket 100 includes a main body 101 connected to a base 102. The base 102 has a backend surface S1 (cannot be seen in FIG. 1A due to limited viewing angle) adapted for attachment to a surface, e.g., the labial surface or lingual surface, of a tooth (not shown). The backend surface S1 can be bonded to a surface of a tooth by adhesive (e.g., light-cure adhesive), for example. Alternatively, the backend surface S1 can be bonded to a mounting base adapted to fit a tooth in a customized setup. The main body 101 has a frontend portion 101A opposite the base 102. The frontend portion 101A has a smooth curved frontend surface S2 opposite the backend surface S1. In some embodiments, when viewed from the frontend surface S2, the gingival access bracket 100 is shaped in rectangular, square, circular, oval, rhombus, parallelogram, or shield shape.

Figure 1B:
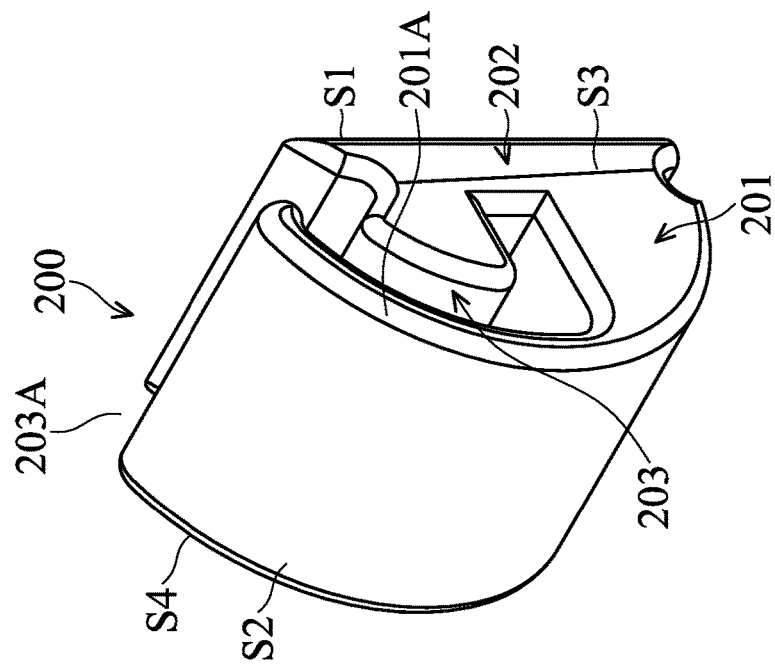
FIG. 1B is a perspective view illustrating a pair of counteracting brackets with rounded edges on their outer surfaces according to some embodiments of the present invention.
Figure 1B:
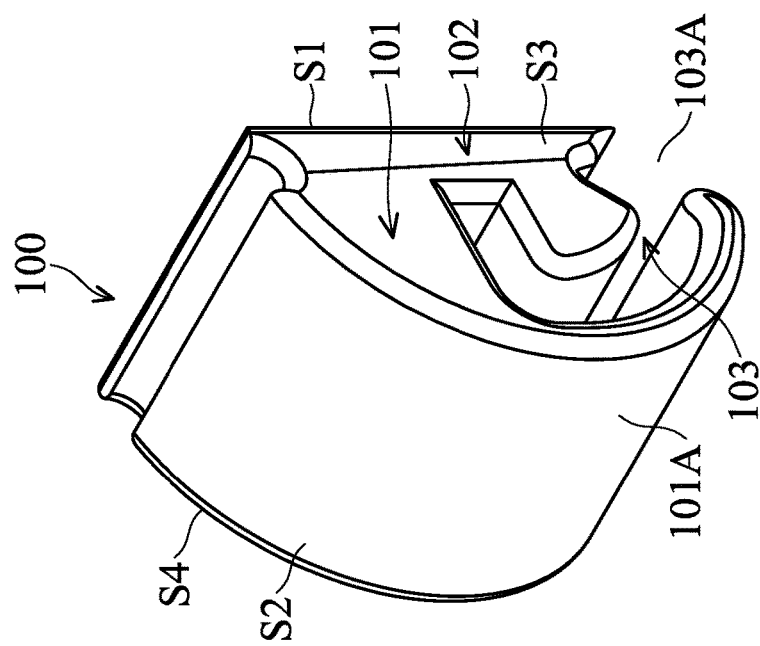

In addition, the main body 101 and the base 102 of the gingival access bracket 100 collectively have two opposite side surfaces S3, S4 (only one side surface S3 can be seen in FIG. 1A due to limited viewing angle) connected between the backend surface S1 and frontend surface S2. In some embodiments, as shown in FIG. 1B, some of the outer surfaces (e.g., the backend surface S1, the frontend surface S2, and/or the side surfaces S3, S4) of the gingival access bracket 100 are designed with rounded edges to minimize discomfort to the patient.

Figure 3A:
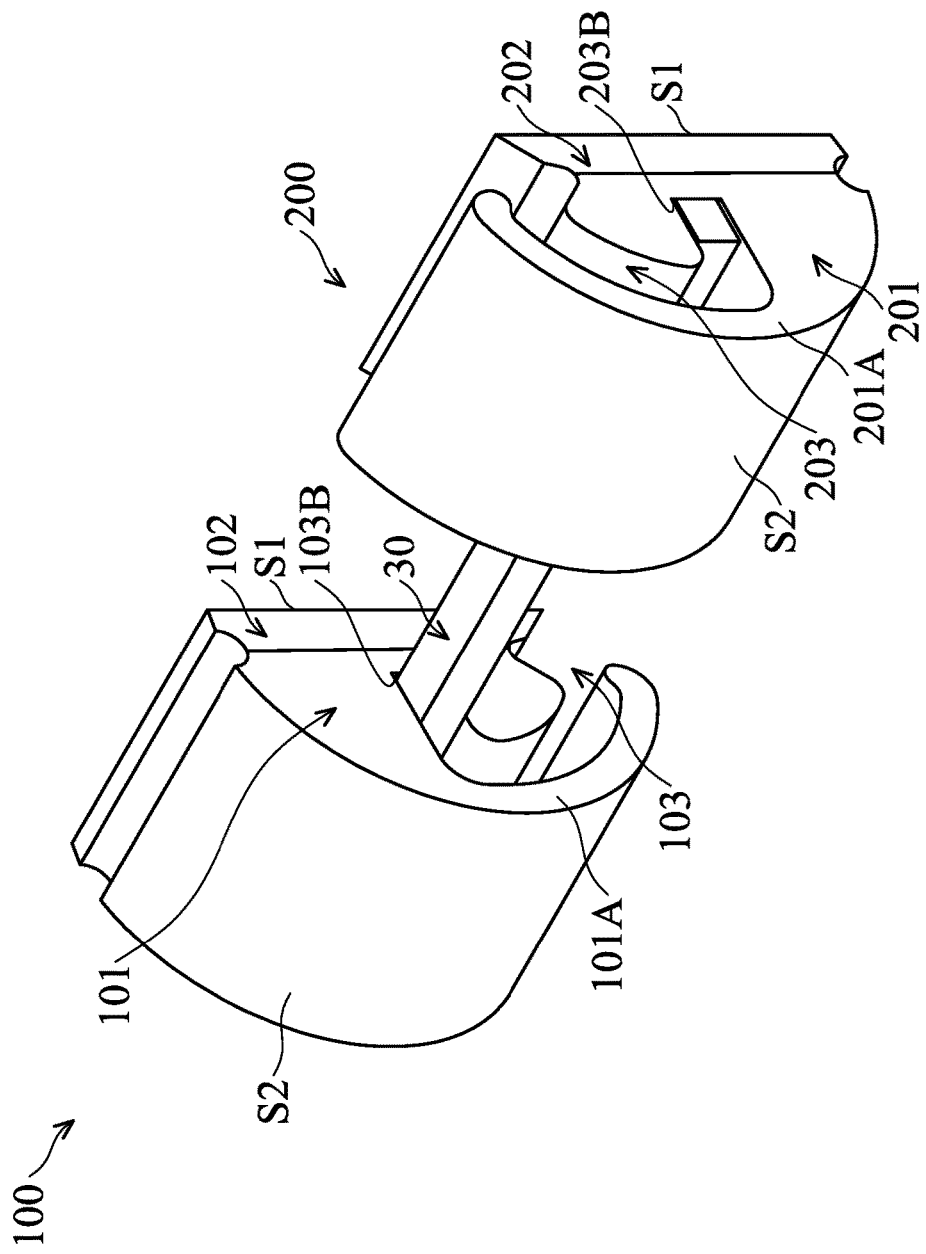
FIG. 3A is a perspective view illustrating an archwire in the archwire slots of the pair of counteracting brackets of FIG. 1A in direct alignment.
Figure 3B:
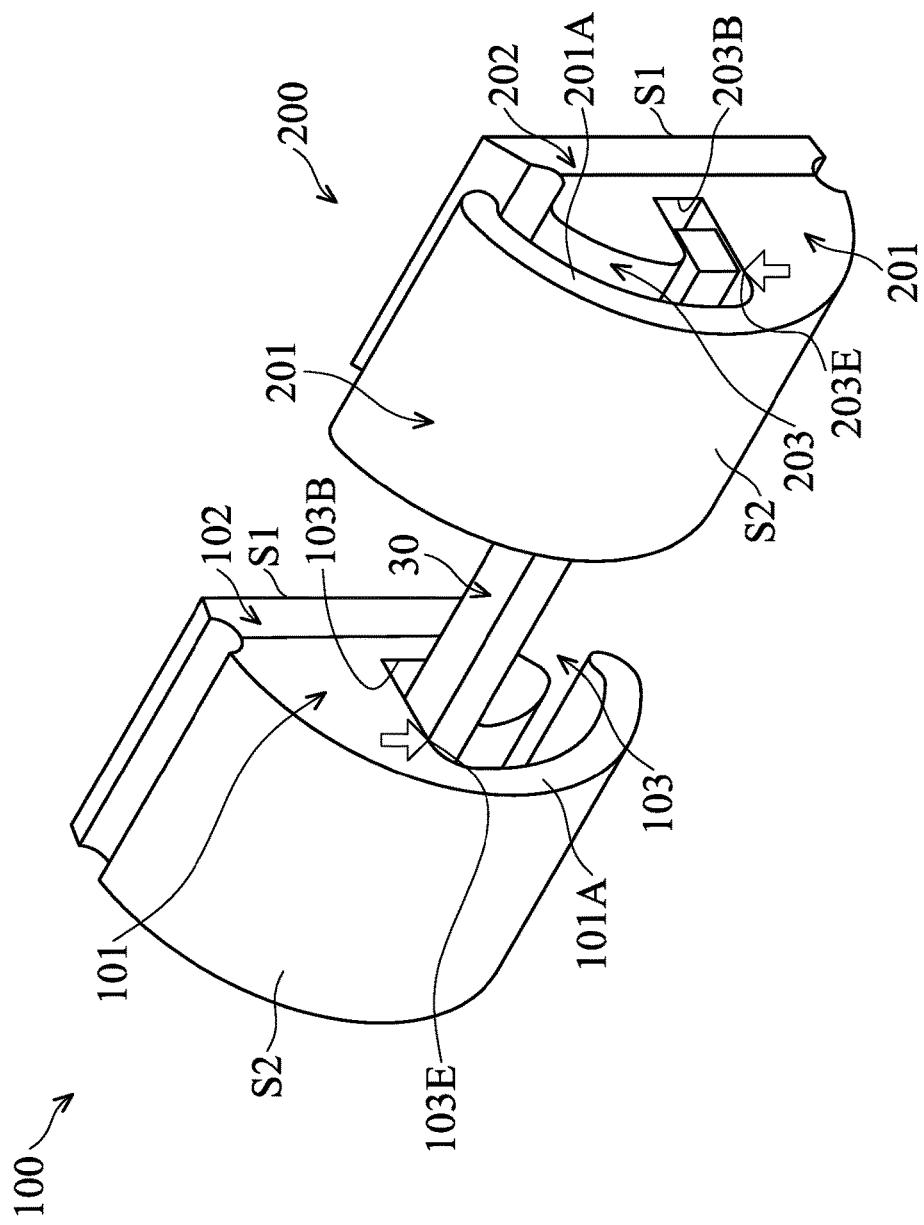
FIG. 3B is a perspective view illustrating an archwire in the archwire slots of the pair of counteracting brackets of FIG. 3A in direct alignment with the archwire in a position of being blocked by the counteracting passageways.

The main body 101 further has a passageway 103 formed therein and extending from the side surface S3 to the side surface S4 for receiving an archwire 30 (see FIGS. 3A and 3B). The passageway 103 forms an access opening 103A on an end of the main body 101 facing toward the gingival direction, for allowing the archwire 30 to enter the passageway 103.

In some embodiments, the main body 101 and the base 102 may comprise the same material, such as metal, metal alloys, ceramics, resins, plastics, or other materials suitable for use in oral applications. In addition, the main body 101 and the base 102 may be integrally formed in one-piece. For example, the main body 101 and the base 102 may be made of a metal material and may be formed in one piece by metal injection molding (MMA). Alternatively, the main body 101 and the base 102 may be individually produced parts with the same or different materials as described above and may be assembled together via adhesive, welding, or other bonding methods. In some alternative embodiments, the main body 101 may also comprise multiple parts and/or multiple materials. Brackets of the present invention may be manufactured in multiple parts, but is assembled to provide the inherent functionality.

Similarly, the occlusal access bracket 200 includes a main body 201 connected to a base 202. The base 202 has a backend surface S1 (cannot be seen in FIG. 1A due to limited viewing angle) adapted for attachment to a surface, e.g., the labial surface or lingual surface, of a tooth (not shown). The backend surface S1 can be bonded to a surface of a tooth by adhesive (e.g., light-cure adhesive), for example. Alternatively, the backend surface S1 can be bonded to a mounting base adapted to fit a tooth in a customized setup. The main body 201 has a frontend portion 201A opposite the base 202. The frontend portion 201A has a smooth curved frontend surface S2 opposite the backend surface S1. In some embodiments, when viewed from the frontend surface S2, the occlusal access bracket 200 is shaped in rectangular, square, circular, oval, rhombus, parallelogram, or shield shape.

In addition, the main body 201 and the base 202 of the occlusal access bracket 200 collectively have two side surfaces S3, S4 (only one side surface S3 can be seen in FIG. 1A due to limited viewing angle) connected between the backend surface S1 and frontend surface S2. In some embodiments, as shown in FIG. 1B, some of the outer surfaces (e.g., the backend surface S1, the frontend surface S2, and/or the side surfaces S3, S4) of the occlusal access bracket 200 are designed with rounded edges to minimize discomfort to the patient.

The main body 201 further has a passageway 203 formed therein and extending from the side surface S3 to the side surface S4 for receiving an archwire 30 (see FIGS. 3A and 3B). The passageway 203 forms an access opening 203A on an end of the main body 201 facing toward the occlusal direction, for allowing the archwire 30 to enter the passageway 203.

The material and manufacturing method of the main body 201 and the base 202 of the occlusal access bracket 200 are similar to the main body 101 and the base 102 of the gingival access bracket 100 and are thus not repeated here.

The gingival access bracket 100 and the occlusal access bracket 200 form a counteracting set. Without specifying the (archwire) access direction, either the gingival access bracket 100 or the occlusal access bracket 200 can be called a counteracting bracket. The counteracting brackets may be used as labial brackets as well as lingual brackets in some embodiments. To achieve the counteracting effect of archwire entrapment, which will be further explained in the following paragraphs, any two adjacent counteracting brackets can be deployed in counteracting pairs where a gingival access bracket is paired with an occlusal access bracket. However, individual bracket can also achieve archwire retention via some features such as a curved passageway (see FIG. 2A) or at least one turn provided in the passageway (see FIG. 4B), without using additional locking clips or closures, in some alternative embodiments.

Figure 2A:
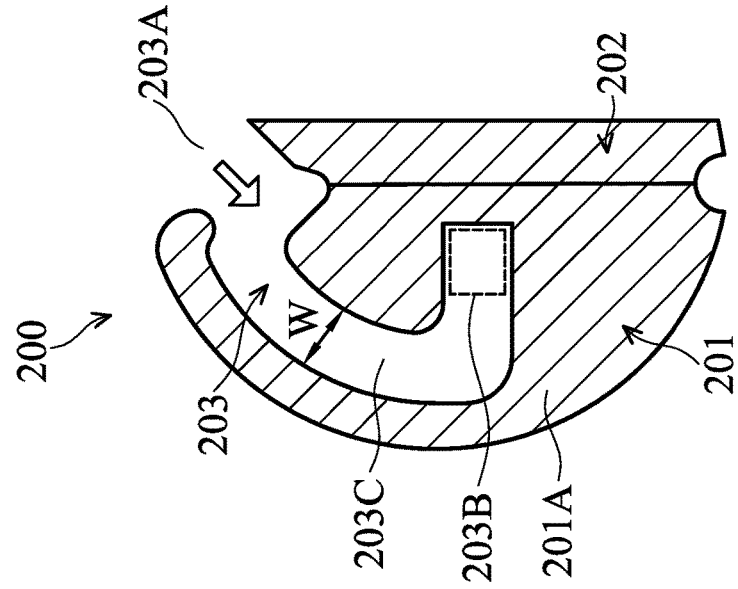
FIG. 2A is a cross-sectional view illustrating the structural features of the pair of counteracting brackets of FIG. 1A.
Figure 2A:
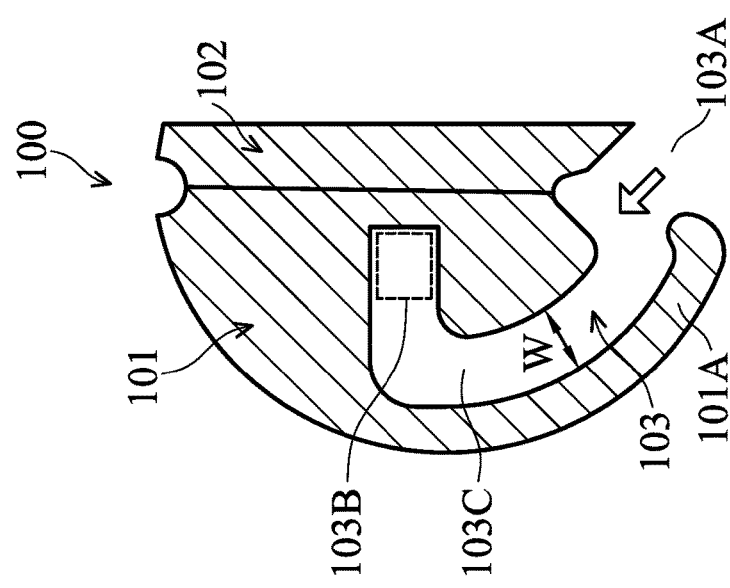

FIG. 2A is a cross-sectional view illustrating the structural features of the pair of counteracting brackets of FIG. 1A. As shown, the cross-section of the passageway 103 of the gingival access bracket 100 is designed to include an access opening 103A, an archwire slot 103B, and a curved path portion 103C. The access opening 103A is configured to allow an archwire 30 (FIGS. 3A and 3B) to enter the passageway 103 (as depicted by an arrow in the figure). The archwire slot 103B is formed at the end of the passageway 103. The curve path portion 103C connects the archwire slot 103B and the access opening 103A. In some embodiments, the curved path portion 103C extends from the archwire slot 103B first toward the frontend portion 101A and then curves back toward the base 102 before bending toward the gingival direction at the access opening 103A. As shown in FIG. 2A, the curved path portion 103C has a width W to allow an archwire 30 to traverse the length of the path portion 103C to be placed or received in the archwire slot 103B. In some embodiments, the width W of the entire path portion 103C is consistent or varied. In some embodiments, an archwire 30 can enter the access opening 103A and follow the curved path portion 103C in a generally clockwise or counterclockwise direction to enter the archwire slot 103B of the gingival access bracket 100.

On the other hand, the cross-section of the passageway 203 of the occlusal access bracket 200 is designed to include an access opening 203A, an archwire slot 203B, and a curved path portion 203C. The configuration, structure, and function of the access opening 203A, archwire slot 203B and path portion 203C are similar to those of the access opening 103A, archwire slot 103B and path portion 103C of the gingival access bracket 100 and are thus not repeated here. In some embodiments, an archwire 30 can enter the access opening 203A and follow the curved path portion 203C in a generally counterclockwise or clockwise direction to enter the archwire slot 203B of the occlusal access bracket 200.

The maximum archwire size allowed is determined by the size of the archwire slots 103B and 203B. In some embodiments, as shown in FIG. 2A, both the archwire slots 103B and 203B have a rectangular cross-section (as depicted by dotted rectangles in the figure) which corresponds to the cross-sectional shape of the received archwire (not shown). However, the archwire slots 103B and 203B can accommodate an archwire with different cross-sectional shapes. For example, an archwire of circular or square cross-sectional shape may also be received in the archwire slots 103B and 203B with rectangular cross-section.

In some embodiments, the width W of the narrowest part of the path portion 103C, 203C is greater than the short side but less than the long side of the rectangular cross-section of an archwire. Accordingly, the archwire is allowed to pass through the path portion 103C and the path portion 203C in a substantially fixed orientation (i.e., without rotation). Moreover, excessive twisting of the archwire during traversal along the path portions 103C and 203C can be avoided.

Figure 2B:
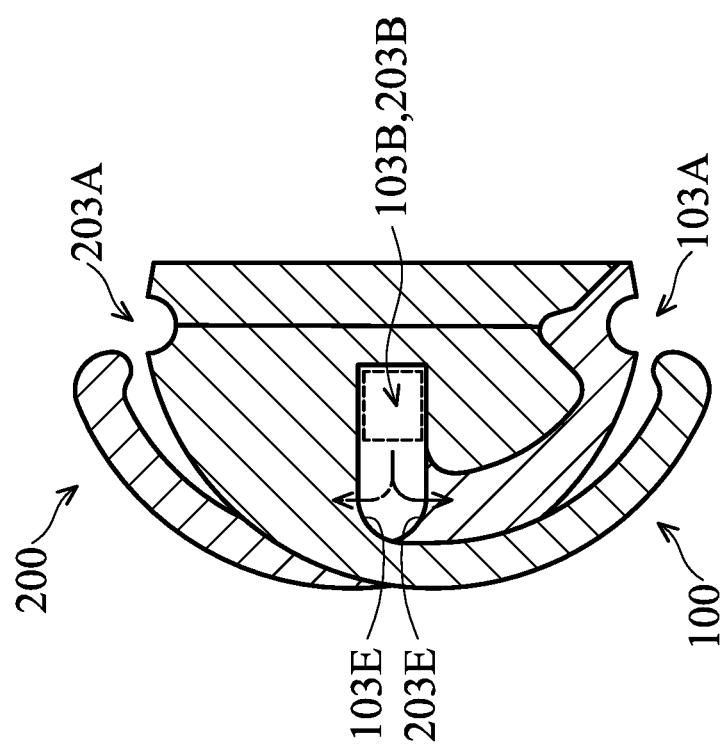
FIG. 2B is a cross-sectional view illustrating an effective archwire slot area based on the counteracting exit passageway directions of the pair of counteracting brackets of FIG. 2A in direct alignment.

FIG. 2B shows an overlap of the cross-sections of the pair of counteracting brackets of FIG. 2A in direct alignment. In particular, the archwire slot 103B of the gingival access bracket 100 is in alignment with the archwire slot 203B of the occlusal access bracket 200. For an archwire (not shown) to exit the archwire slot 103B, it needs to follow the path portion 103C of the gingival access bracket 100 in the exit direction indicated by a solid arrow in FIG. 2B. However, the archwire is prevented from exiting by the passageway wall 203E of the occlusal access bracket 200. On the other hand, for the archwire to exit the archwire slot 203B, it needs to follow the path portion 203C of the occlusal access bracket 200 in the exit direction indicated by a dashed arrow in FIG. 2B. Again, the archwire is prevented from exiting by the passageway wall 103E of the gingival access bracket 100. As a result, the overlap of the passageway walls 103E and 203E forms an effective archwire slot area when the cross-sections of the counteracting brackets 100 and 200 are in direct alignment. The combined effect of two adjacent brackets in a basic counteracting pair maintains the archwire in the archwire slots without a clip or closure mechanism.

FIG. 3A is a perspective view illustrating an archwire in the archwire slots of the pair of counteracting brackets of FIG. 1A in direct alignment. As shown, after installation, an archwire 30 is placed in the archwire slot 103B of the gingival access bracket 100 and in the archwire slot 203B of the occlusal access bracket 200, wherein the two brackets are in direct alignment. In some embodiments, the archwire 30 is a thermal Nickel-Titanium (Ni—Ti) wire, which is flexible at room temperature and can be easily installed by the doctor or patient. In actual deployment to a dental arch, some adjacent brackets are lined up along a curve while others are in irregular positions. Furthermore, the backend surface S1 of the bracket 100, 200 can be designed with different tilt angles and/or shapes to fit different shapes of teeth, or the backend surface S1 of the bracket 100, 200 can be attached to a customized mounting base adapted to fit a tooth's surface, so that those brackets are in alignment.

FIG. 3B shows the situation where the archwire 30 shifts toward the frontend portions 101A and 201A of the brackets 100 and 200. Arrows depicted in the figure indicate that the archwire 30 comes into contact with the passageway walls 103E and 203E. As a result, the archwire 30 is prevented from exiting the passageways 103 and 203, thereby achieving the counteracting effect of archwire entrapment without using a clip or closure mechanism.

Figure 4A:
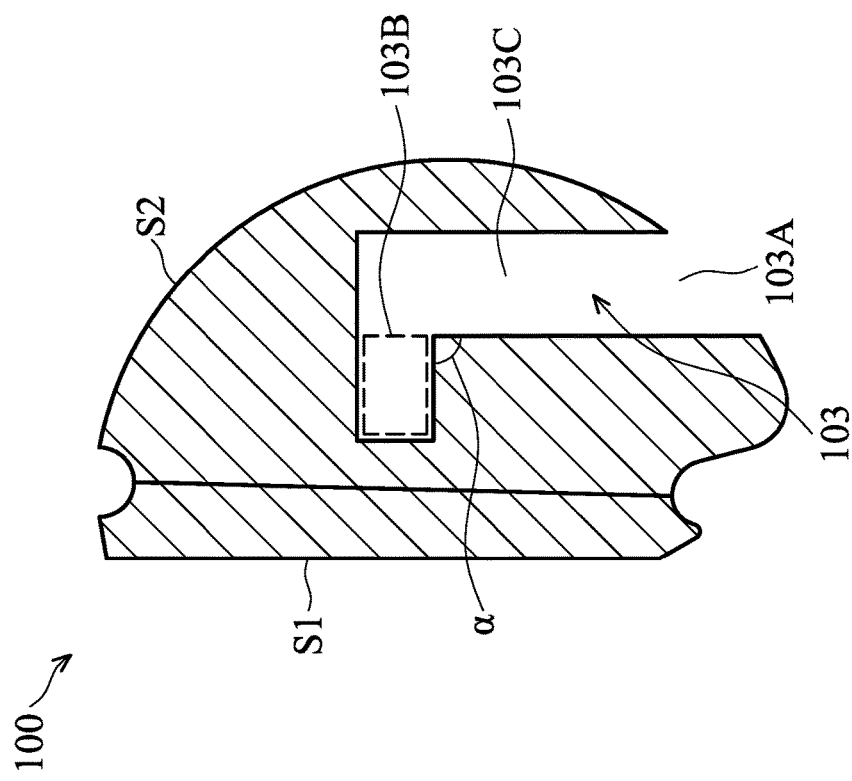
FIG. 4A is a cross-sectional view illustrating the structural features of a counteracting bracket according to some embodiments of the present invention.
Figure 4B:
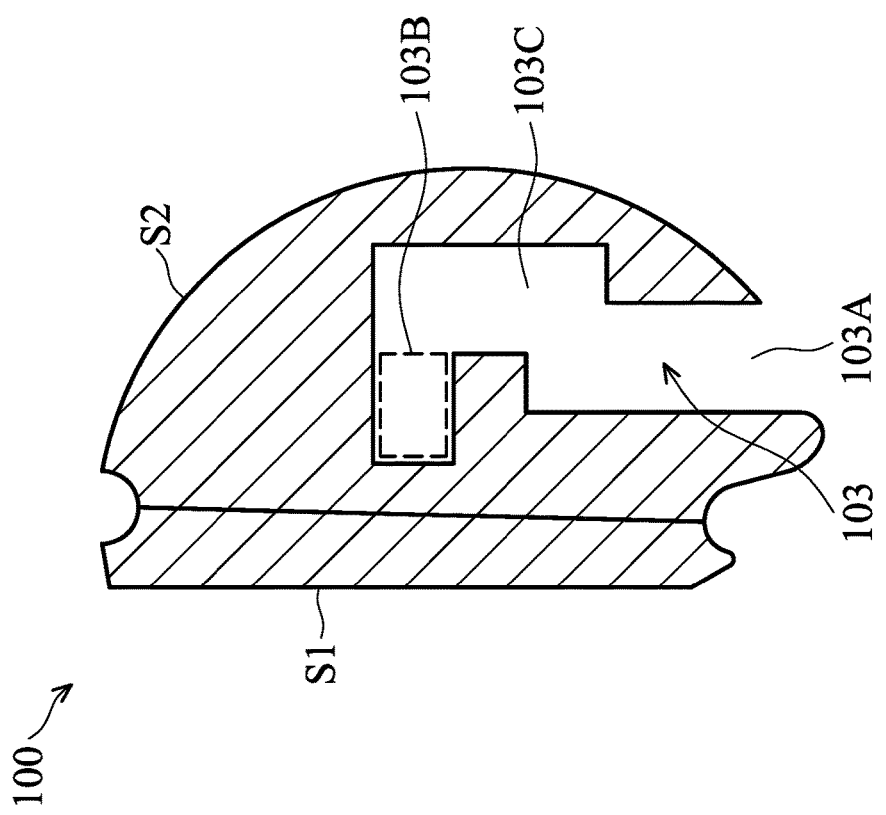
FIG. 4B is a cross-sectional view illustrating the structural features of a counteracting bracket according to some embodiments of the present invention.

It should be appreciated that many variations and modifications can be made to the embodiments of the present disclosure. For example, FIGS. 4A and 4B are cross-sectional views illustrating various structural features of a counteracting bracket (a gingival access bracket 100 is used as an example for illustrate) according to some alternative embodiments. As shown in FIG. 4A, the path portion 103C of the passageway 103 is designed to be straight in cross-section, and an angle α such as about 90 degrees is formed between the path portion 103C and the archwire slot 103B (i.e. the straight path portion 103C is designed to be substantially perpendicular to the archwire slot 103B). However, the angle α may also have another available degrees (e.g., more than about 30 degrees). As shown in FIG. 4B, the path portion 103C of the passageway 103 is designed to include at least one turn or bending design in cross-section. The turn or turns provided in the path portion 103C prevent a received archwire from escaping easily from the passageway 103 spontaneously.

Figure 5A:
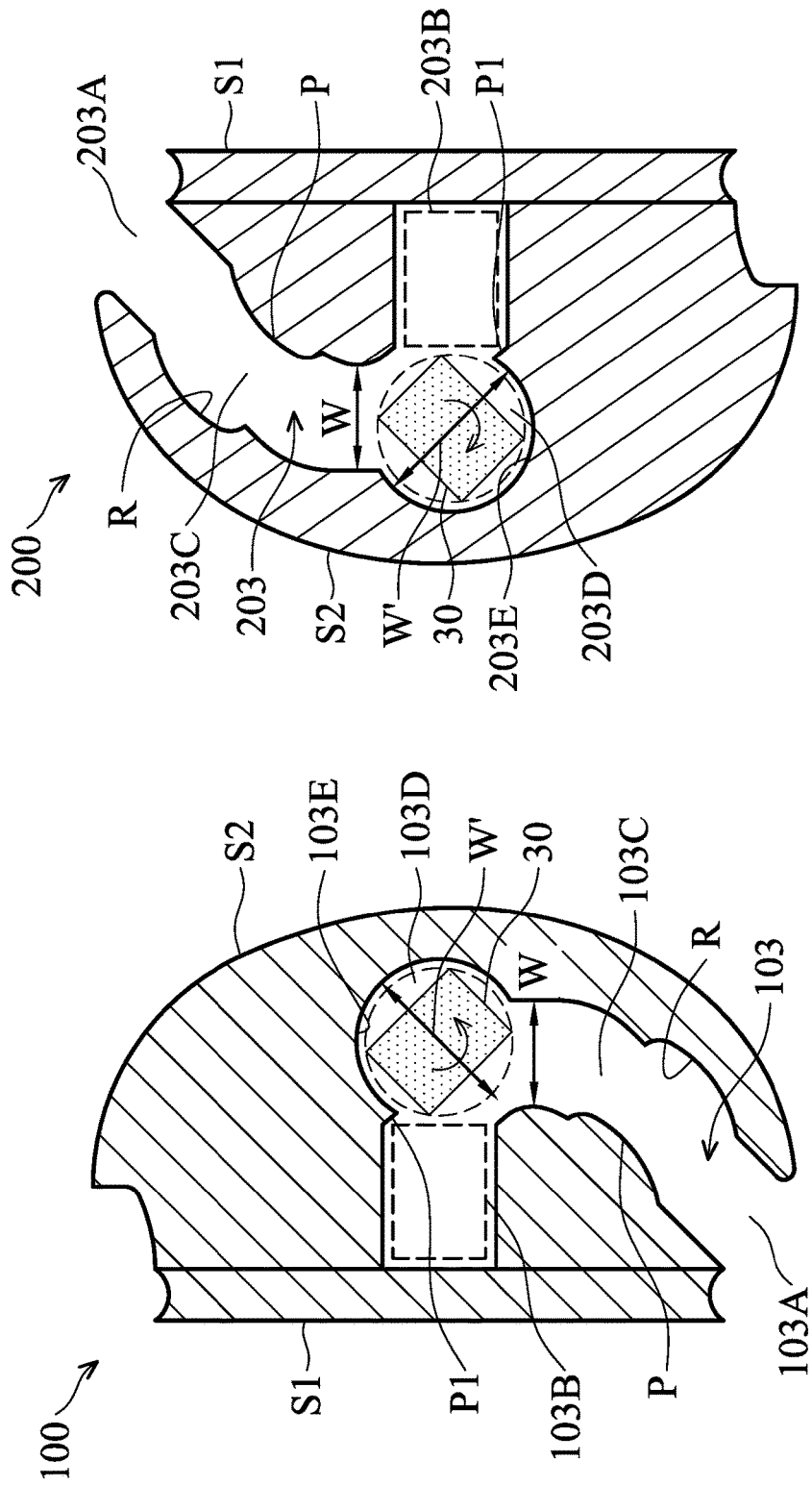
FIG. 5A is a cross-sectional view illustrating the structural features of a pair of counteracting brackets according to some embodiments of the present invention.

FIG. 5A is a cross-sectional view illustrating the structural features of a pair of counteracting brackets according to some alternative embodiments. As shown, compared with the embodiment shown in FIG. 2A, the cross-section of the passageway 103 of the gingival access bracket 100 further includes a rotation portion 103D provided in the curved path portion 103C, and the cross-section of the passageway 203 of the occlusal access bracket 200 further includes a rotation portion 203D provided in the curved path portion 203C. In some embodiments, the rotation portion 103D, 203D may be circular in cross-section as shown in FIG. 5A, but the invention is not limited thereto.

The rotation portions 103D and 203D are configured to allow an archwire 30 to rotate to change its orientation (the dotted circles in the passageways 103 and 203 depicted in the figure represents that the archwire 30 may rotate in the rotation portions 103D and 203D) before entering the archwire slots 103B and 203B. In some embodiments, the width W' of the rotation portion 103D (e.g. the diameter of the circular rotation portion 103D) is greater than the (maximum) width W of the path portion 103C, and the width W' of the rotation portion 203D (e.g. the diameter of the circular rotation portion 203D) is greater than the (maximum) width W of the path portion 203C, so as to allow the archwire 30 to change its orientation. In addition, the rotation portion 103D may be positioned near the archwire slot 103B or at any position of the path portion 103C, and the rotation portion 203D may be positioned near the archwire slot 203B or at any position of the path portion 203C.

Figure 6:
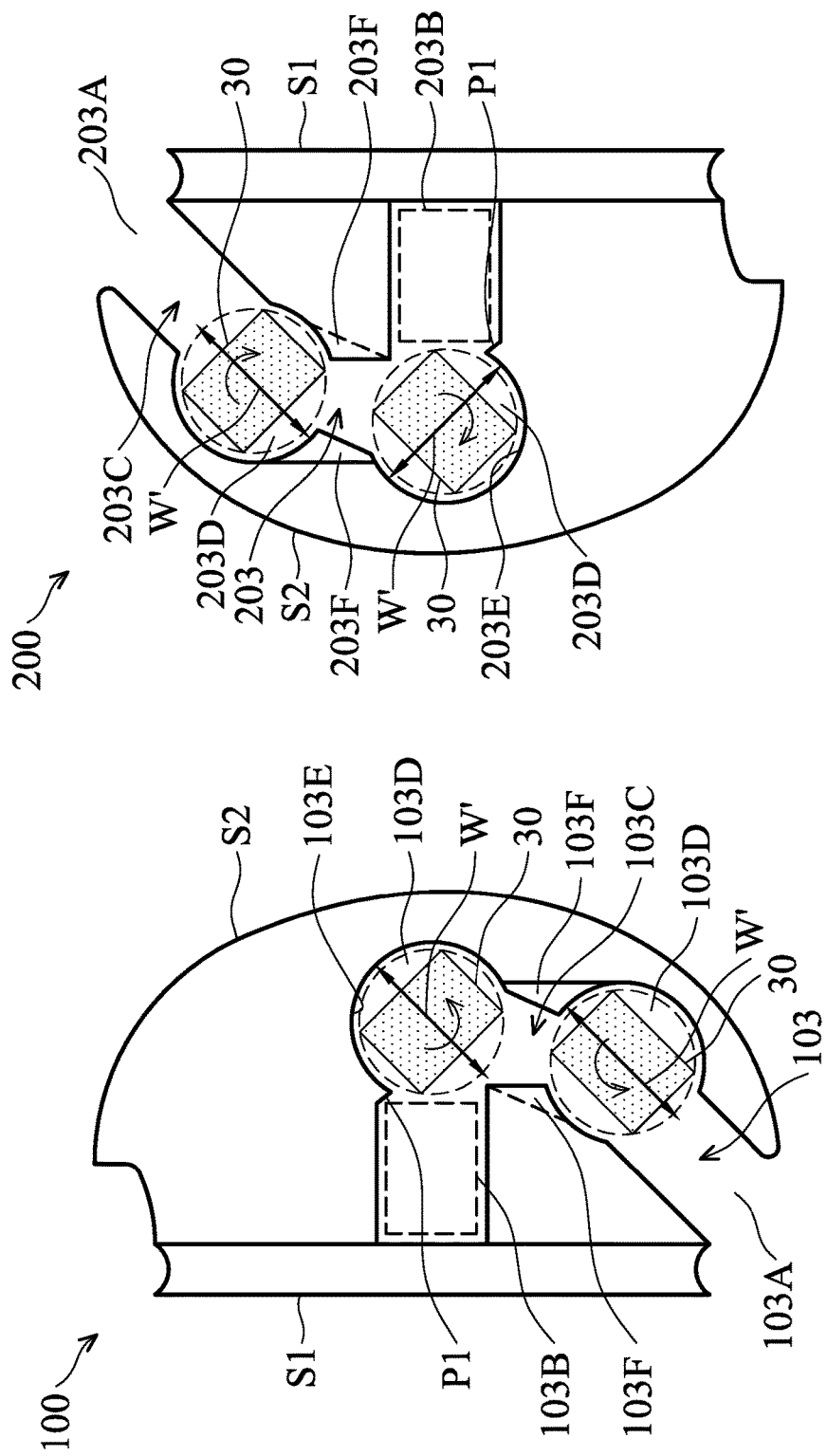
FIG. 6 is a side view illustrating the structural features of a pair of counteracting brackets according to some embodiments of the present invention.

In some alternative embodiments, as shown in FIG. 6, the cross-section of the passageway 103 of the gingival access bracket 100 may further include a plurality of (e.g., two or more than two) rotation portions 103D separately formed in the path portion 103C, and the cross-section of the passageway 203 of the occlusal access bracket 200 may further include a plurality of (e.g., two or more than two) rotation portions 203D separately formed in the path portion 203C, to allow an archwire 30 to rotate to change its orientation.

Accordingly, the doctor or patient can manually turn segments of the archwire 30 to their original orientations at the rotation portions 103D and 203D, so that the stress loading on the archwire 30 due to twisting is released before the archwire 30 enters the archwire slots 103B and 203B.

It should be appreciated that the above design of the rotation portions 103D and 203D may also be integrated with the embodiments as described above. On the other hand, in the cases of no rotation portion provided in the path portion 103C, 203C of the bracket 100, 200 (e.g., the embodiments shown in FIGS. 2A to 4B), the path portion 103C, 203C may also be designed to have a sufficient width to allow an archwire 30 to change its orientation freely during traversal from the access opening 103A, 203A to the archwire slot 103B, 203B along the path portion 103C, 203C (that is to say, the path portion 103C, 203C with a sufficient width can also achieve the function of the rotation portion).

In addition, as shown in FIG. 6, the passageway wall 103E of the passageway 103 and the passageway wall 203E of the passageway 203 may respectively have at least one portion that is tilted with respect to the extension direction of the passageway 103 and the passageway 203 (i.e. the direction into the paper as shown in the figure) to form an uneven surface 103F, 203F. The uneven surface 103F, 203F requires an archwire 30 to be manipulated to twist, thereby increasing the difficulty for the archwire 30 to pass through this section of the passageway 103, 203 to prevent the archwire 30 from escaping easily from the passageway 103, 203 spontaneously.

In some embodiments of the present invention (see FIG. 5A), at least one protrusion P is formed on a side of the path portion 103C, 203C of the bracket 100, 200, and at least one depression R is formed on the other side of path portion 103C, 203C to correspond to the protrusion P. During the installation of an archwire 30, the doctor or patient can manipulate the archwire 30 to go around the protrusion P of the bracket 100, 200 to enter the archwire slot 103B, 203B. The protrusion P is configured to prevent an archwire 30 received in the archwire slot 103B, 203B from escaping easily from the passageway 103, 203 spontaneously. In some embodiments, the protrusion P may be a bump or island structure positioned near the side surface S3, S4, or between the side surfaces S3 and S4 (FIG. 1A) of the bracket 100, 200. In some alternative embodiments, the path portion 103C and/or 203C may have multiple protrusions P.

Figure 5B:
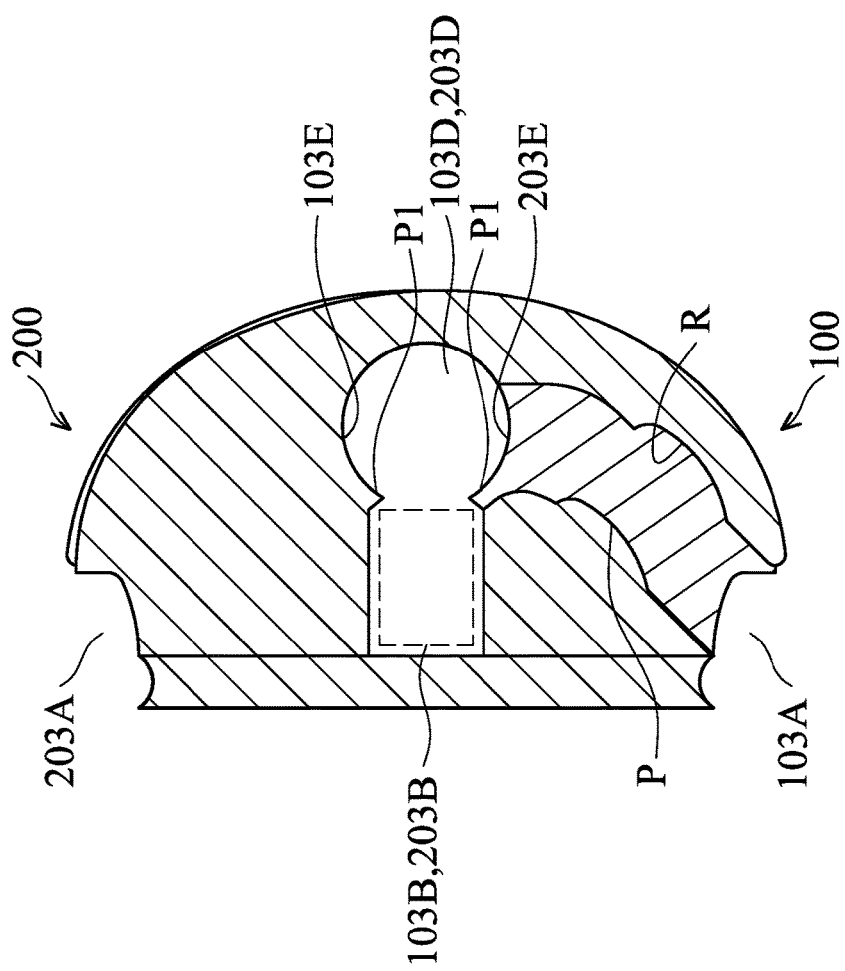
FIG. 5B is a cross-sectional view illustrating an effective archwire slot area based on the counteracting exit passageway directions of the pair of counteracting brackets of FIG. 5A in direct alignment.

FIG. 5B shows an overlap of the cross-sections of the pair of counteracting brackets of FIG. 5A in direct alignment, wherein another protrusion P1 is also provided in the path portions 103C and 203C and positioned between the archwire slot 103B, 203B and the rotation portion 103D, 203D to lead to a reduction of the size of the effective archwire slot area that is formed by the passageway walls 103E and 203E, so that an archwire 30 can be well confined in the effective archwire slot area without using additional locking clips or closures. It should be appreciated that the above designs of the protrusion P and/or the protrusion P1 may also be integrated with other embodiments of the present invention as described above.

Figure 7:
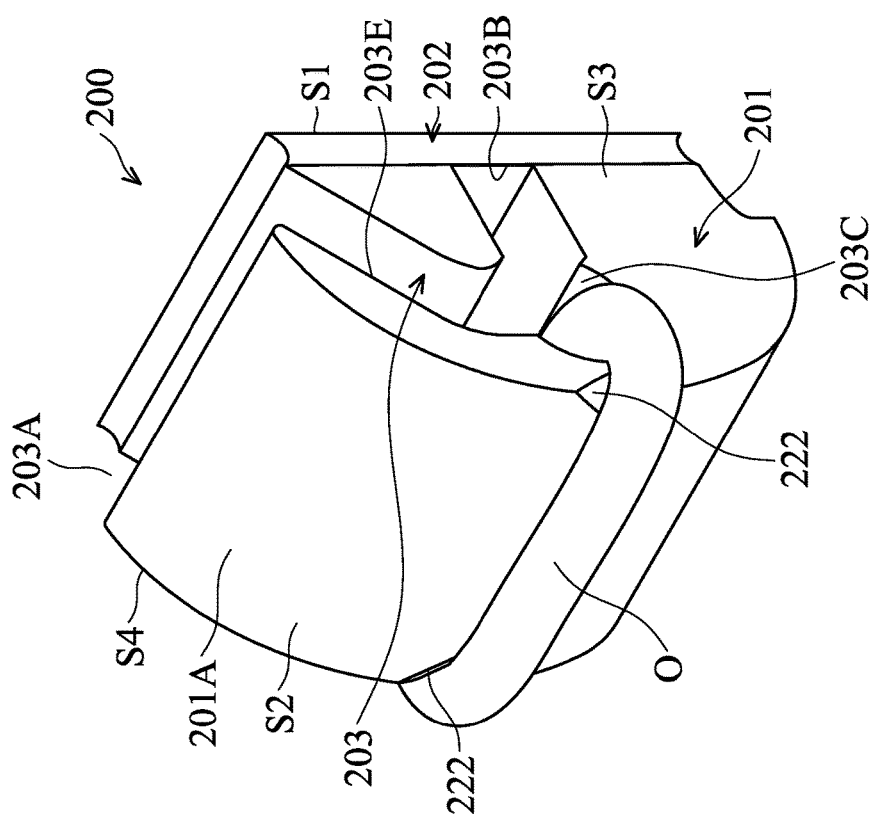
FIG. 7 is a perspective view illustrating a counteracting bracket with O-ring notches according to some embodiments of the present invention.

FIG. 7 is a perspective view illustrating a counteracting bracket (an occlusal access bracket 200 is used as an example for illustration) with O-ring notch features according to some alternative embodiments. As shown, a pair of O-ring notches 222 is formed on the side surfaces S3 and S4 of the frontend portion 201A near the frontend surface S2. Alternatively or additionally, another pair of O-ring notches 222 (not shown) may be formed on the side surfaces S3 and S4 of the frontend portion 201A near the passageway wall 203E. An O-ring elastic O, such as a rubber O-ring, can be easily retained by the O-ring notches 222.

In some embodiments, the O-ring notches 222 are positioned near the archwire slot 203B, as shown in FIG. 7. By installing an O-ring elastic O at this position, an additional barrier is created in the passageway 203 to keep an archwire (not shown) in the archwire slot 203B. This feature allows a counteracting bracket to be used in single bracket applications. Also, deployment of counteracting brackets to a dental arch may encounter a situation of severe positional (or level) discrepancies between adjacent brackets that requires an O-ring elastic O to ensure entrapment of the archwire in the archwire slot 203B. It should also be appreciated that the O-ring notches 222 may also allow the deployment of counteracting brackets in other configurations with multiple brackets, as long as the O-ring elastic O can be retained by the O-ring notches 222 to prevent an archwire from escaping the archwire slot 203B.

Figure 8:
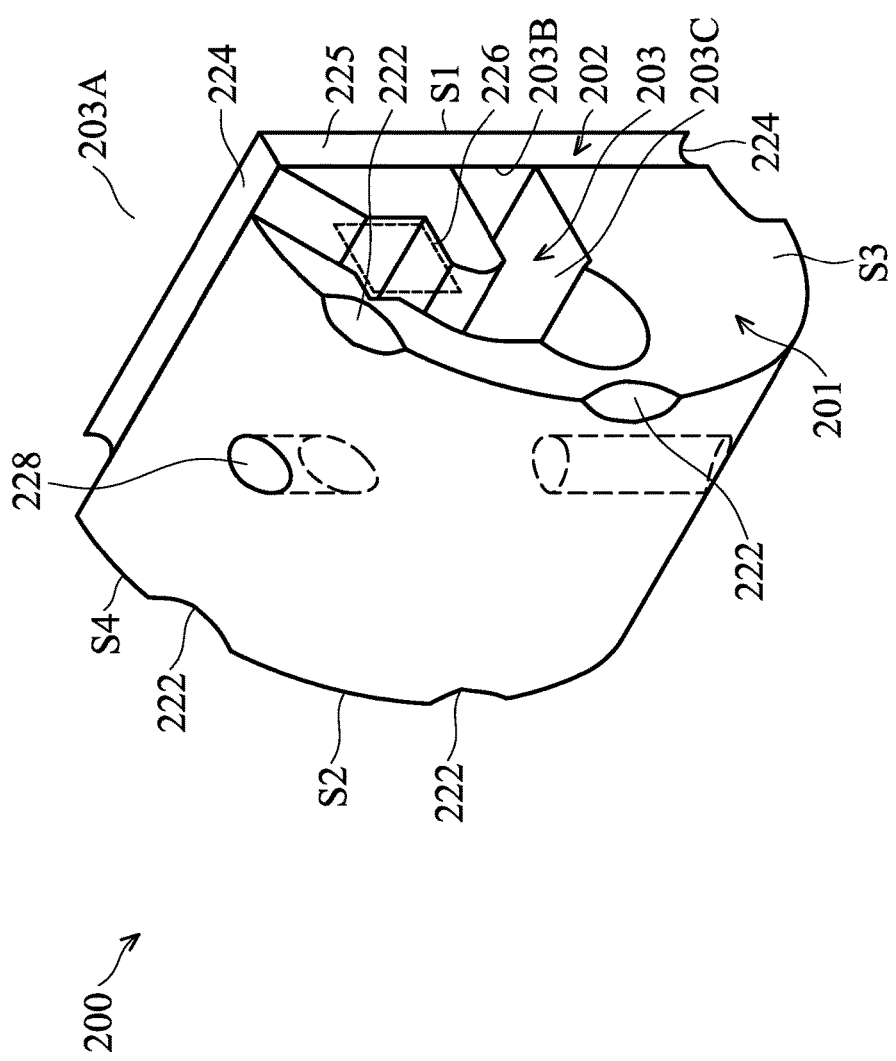
FIG. 8 is a perspective view illustrating a counteracting bracket with an auxiliary archwire slot, grooves on four sides, and an auxiliary device slot according to some embodiments of the present invention.

FIG. 8 is a perspective view illustrating a counteracting bracket (an occlusal access bracket 200 is used as an example for illustration) with additional features, including an auxiliary archwire slot, grooves on four sides, and an auxiliary device slot, according to some alternative embodiments. As shown, an occlusal access bracket 200 includes an auxiliary archwire slot 226 (as depicted by a dotted rectangle in the figure) in addition to the archwire slot 203B. The auxiliary archwire slot 226 is formed in the path portion 203C of the passageway 203, parallel to the archwire slot 203B, for accommodating an auxiliary archwire (not shown in the figure for the purpose of simplicity and clarity). In some embodiments, the auxiliary archwire slot 226 has similar structure and size with the archwire slot 203B, and/or the auxiliary archwire has similar structure and size with the archwire 30 (FIGS. 3A-3B). The auxiliary archwire slot 226 allows an auxiliary archwire to be installed in the case of lingual brackets to compensate for the positional (or level) offset between canines and first premolars, for example. Alternatively, an auxiliary archwire slot 226 may be formed in the body of the bracket, in a position away from the passageway 203 and the archwire slot 203B.

To keep an auxiliary archwire in the auxiliary archwire slot 226, two O-ring elastics O (not shown in the figure for the purpose of simplicity and clarity) can be installed in the O-ring notches 222 near the auxiliary archwire slot 226 (for example, a pair of O-ring notches 222 above and another pair of O-ring notches 222 below the auxiliary archwire slot 226). However, it should be appreciated that many variations and modifications can be made to the embodiments of the disclosure.

Figure 9:
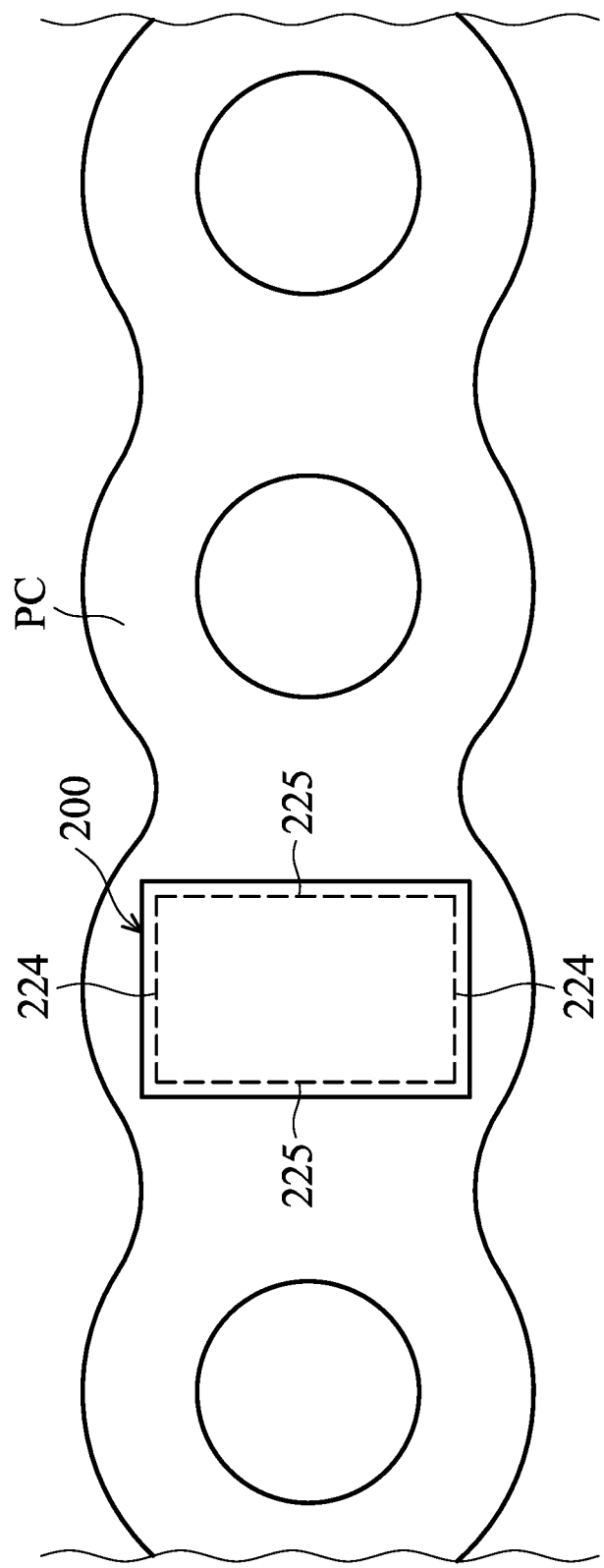
FIG. 9 schematically shows that a power chain is installed on the counteracting bracket shown in FIG. 8.

Still referring to FIG. 8, the occlusal access bracket 200 further includes two power chain grooves 224 formed on opposing ends (facing toward the occlusal and gingival directions) of the occlusal access bracket 200, parallel to the archwire slot 203B, and positioned between the archwire slot 203B and the backend surface S1, for receiving or retaining a power chain elastic PC (see FIG. 9) that is commonly used for orthodontic treatment. Alternatively or additionally, the occlusal access bracket 200 may include two power chain grooves 225 formed on the side surfaces S3, S4 (only one power chain groove 225 formed on the side surface S3 can be seen in FIG. 8 due to limited viewing angle) and positioned between the archwire slot 203B and the backend surface S1 for receiving or retaining a power chain elastic PC. In some embodiments, the power chain grooves 224 and 225 may also be used to accommodate another type of orthodontic elastic. Note that the power chain grooves 224 and/or 225 are positioned a certain distance from the archwire slot 203B near the backend surface S1, which prevents an installed power chain from contacting an archwire in the archwire slot 203B.

Figure 10:
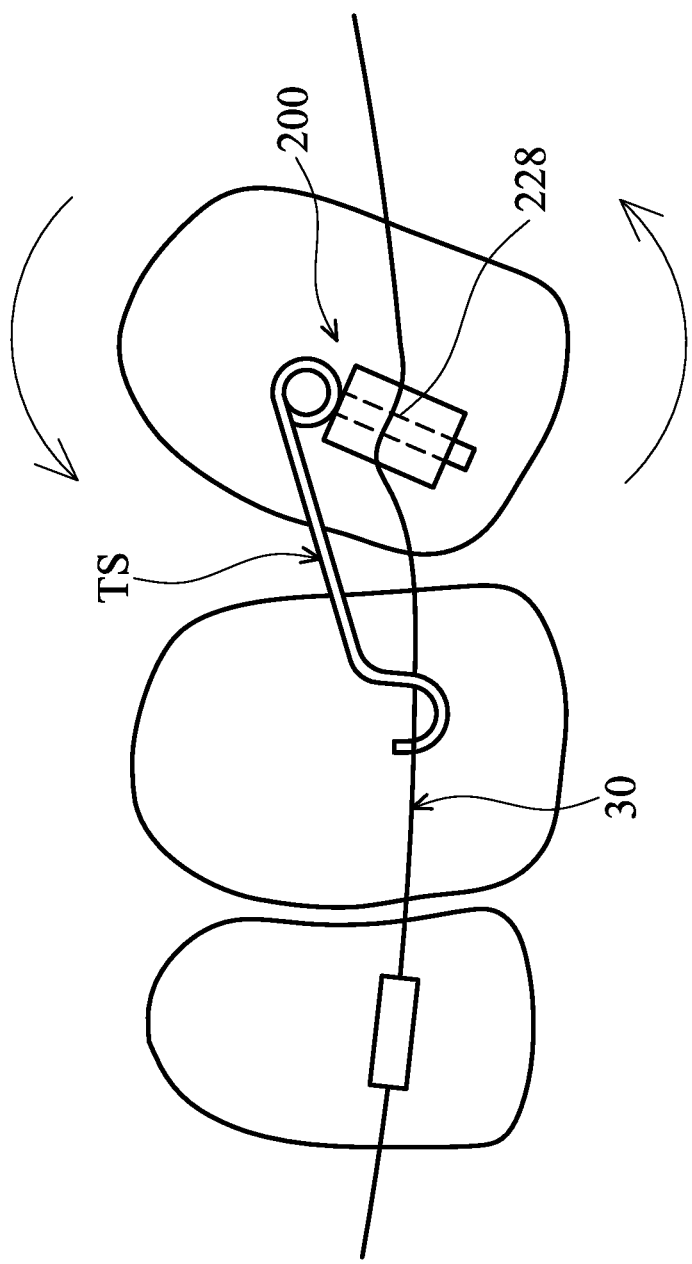
FIG. 10 schematically shows that an uprighting spring is attached to a counteracting bracket for uprighting a tipped tooth.

As shown in FIG. 8, the occlusal access bracket 200 further includes an auxiliary device slot 228 formed therein. In some embodiments, the auxiliary device slot 228 is extended from an end of the occlusal access bracket 200 (e.g. an end of the occlusal access bracket 200 near the access opening 203A) to its interior or further to extend to the opposite end of the occlusal access bracket 200. Moreover, the auxiliary device slot 228 may be positioned a certain distance behind or in front of the archwire slot 203B, and it provides a means to attach an auxiliary device to the orthodontic bracket. One application is to attach an uprighting spring TS to the auxiliary device slot 228 (see FIG. 10), so as to apply a force by the uprighting spring TS to the archwire 30 and the connected brackets (not shown), thereby uprighting tipped tooth or teeth. An uprighting spring TS is commonly used in orthodontics and is thus not illustrated further. It should be noted that the uprighting spring TS received in the auxiliary device slot 228 does not contact or affect an archwire in the archwire slot 203B. In some embodiments, an extended base portion is formed below the power chain grooves 224 with a thickness sufficient to allow an auxiliary device slot 228 to pass through it, wherein the auxiliary device slot 228 passes below the power chain grooves 224.

Figure 11:
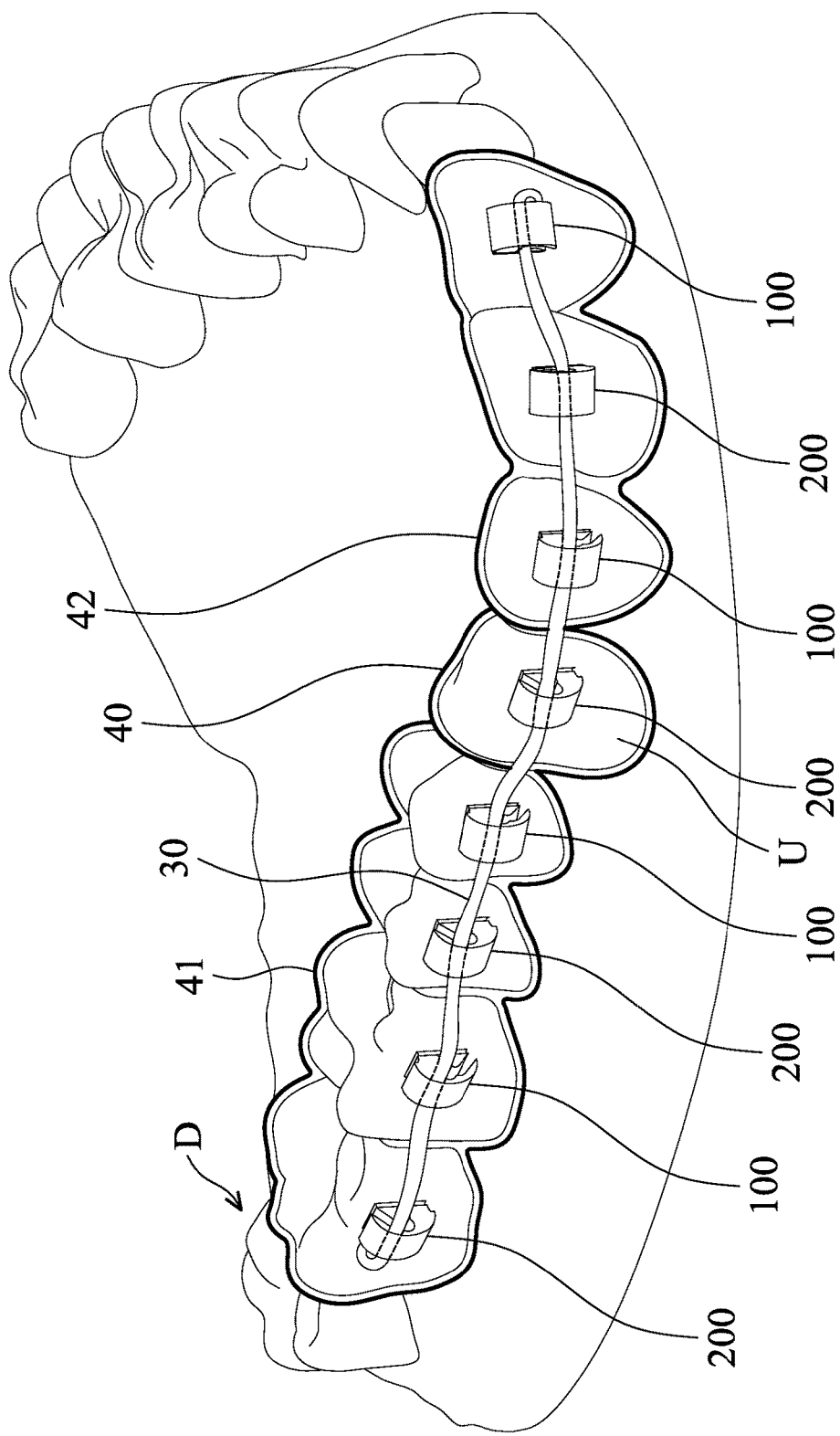
FIG. 11 is a perspective view illustrating an application of counteracting brackets to a patient removable appliance consisting of tooth cap segments, according to some embodiments of the present invention.

In addition to fixed braces applications, the counteracting brackets described above can also be used in patient removable appliances. FIG. 11 is a perspective view illustrating an application of counteracting brackets to a patient removable appliance consisting of tooth cap segments, according to some embodiments of the present invention. As shown, the appliance includes three tooth cap segments, including a first anchorage segment 41, a second anchorage segment 42, and an uprighting tooth cap 40. The uprighting tooth cap 40 is installed on a tooth U which requires uprighting correction. The first anchorage segment 41 and the second anchorage segment 42 respectively have several counteracting brackets 100 and 200 fixed to the tooth cap segment surface. The uprighting tooth cap 40 has a counteracting bracket 100 or 200 fixed to the uprighting tooth cap surface. It should be appreciated that any pair of adjacent counteracting brackets 100 and 200 have counteracting exit passageways as described above.

The procedure to install the appliance is as follow. First, the uprighting tooth cap 40, the first and second anchorage segments 41 and 42 are installed on the dental arch D without an archwire attached. Next, segments of the archwire 30 are installed on the counteracting brackets 100 and 200 of the uprighting tooth cap 40, the first and anchorage segment 41 and 42. The archwire installation can be performed by the patient easily due to the counteracting brackets. In some embodiments, the tooth cap segments 40, 41, and 42 may be comprised of segments of aligners, retainers or positioners.

As described above, the counteracting bracket of the present disclosure improves upon the conventional self-ligating bracket in terms of construction, ease of use and patient discomfort. The counteracting bracket has a simplified design without a locking clip or closure mechanism. The dental professional is released from the demanding task of manipulating tiny locking clips or closure mechanisms. Finally, with the removal of additional edges and protrusions of a locking clip or closure mechanism, a simple and easy-to-use bracket is created with smooth surfaces and rounded edges, which reduces patient discomfort. In another aspect, the ease of use also allows the counteracting bracket to be applied in patient removable appliances.

Although embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. A dental appliance, comprising: an archwire configured to apply corrective force to a tooth, wherein the archwire has a rectangular cross-section; and an orthodontic bracket, comprising: a backend surface adapted for attachment; a frontend surface opposite the backend surface; a first side surface connected between the backend surface and the frontend surface; a second side surface connected between the backend surface and the frontend surface, opposite the first side surface; and a passageway extending from the first side surface to the second side surface, the cross-section of the passageway including an access opening, an archwire slot, a path portion, and at least one circular rotation portion, wherein the access opening is configured to allow the archwire to enter the passageway, the archwire slot is formed at the end of the passageway to receive the archwire, and the path portion connects the access opening and the archwire slot, the path portion and archwire slot being not in alignment, wherein a width of a narrowest part of the path portion is greater than a short side but less than a long side of the rectangular cross-section of the archwire, wherein the archwire has a rectangular cross-section, and the circular rotation portion is provided in the path portion and has a diameter large enough to accommodate a diagonal length of the rectangular cross-section of the archwire so as to allow the archwire to rotate and change its orientation.

2. The dental appliance as claimed in claim 1, wherein the frontend surface is a smooth curved surface.

3. The dental appliance as claimed in claim 1, wherein the backend surface, the frontend surface, the first side surface, and/or the second side surface are designed with rounded edges.

4. The dental appliance as claimed in claim 1, wherein the diameter of the circular rotation portion is greater than the width of the path portion.

5. The dental appliance as claimed in claim 1, wherein the path portion is curved.

6. The dental appliance as claimed in claim 1, wherein the path portion is straight.

7. The dental appliance as claimed in claim 1, wherein the path portion includes at least one turn.

8. The dental appliance as claimed in claim 1, wherein the passageway further includes a plurality of circular rotation portions separately provided in the path portion.

9. The dental appliance as claimed in claim 1, wherein the archwire slot has a rectangular cross-section.

10. The dental appliance as claimed in claim 1, wherein the passageway further includes at least one portion that is tilted with respect to an extension direction of the passageway to form an uneven surface, for preventing the archwire from escaping from the passageway easily.

11. The dental appliance as claimed in claim 1, wherein the cross-section of the passageway further includes a protrusion formed in the path portion, for preventing the archwire from escaping from the archwire slot easily.

12. The dental appliance as claimed in claim 1, wherein the orthodontic bracket further comprises at least one notch formed on the first side surface and/or the second side surface, for retaining an O-ring elastic.

13. The dental appliance as claimed in claim 1, wherein the passageway further includes at least one auxiliary archwire slot provided in the path portion, parallel to the archwire slot, for accommodating at least one auxiliary archwire.

14. The dental appliance as claimed in claim 1, wherein the orthodontic bracket further comprises at least two grooves formed on opposing ends of the orthodontic bracket and positioned between the archwire slot and the backend surface, for receiving a power chain elastic.

15. The dental appliance as claimed in claim 1, wherein the orthodontic bracket further comprises at least one auxiliary device slot extending from an end of the orthodontic bracket to its interior, for receiving an uprighting spring.

* * * * *